United States Patent [19]

Tanaka et al.

[11] Patent Number: 5,411,731
[45] Date of Patent: May 2, 1995

[54] BATH ADDITIVE COMPOSITION COMPRISING ALUMINUM SALT AND CARBONATE OR BICARBONATE WHICH YIELDS A BATH WATER OF PH 8 TO 9

[75] Inventors: Norihiro Tanaka, Kaminokawa; Kazuyuki Okui, Ichikai; Yasuhiro Doi, Ishibashi; Hirotaka Sato; Hidenori Yorozu, both of Utsunomiya, all of Japan

[73] Assignee: Kao Corporation, Tokyo, Japan

[21] Appl. No.: 94,441

[22] Filed: Jul. 21, 1993

[30] Foreign Application Priority Data

| Jul. 21, 1992 | [JP] | Japan | 4-194121 |
| Aug. 18, 1992 | [JP] | Japan | 4-219320 |
| Feb. 24, 1993 | [JP] | Japan | 5-035313 |
| Feb. 24, 1993 | [JP] | Japan | 5-035314 |
| Feb. 26, 1993 | [JP] | Japan | 5-038389 |
| Feb. 26, 1993 | [JP] | Japan | 5-038391 |

[51] Int. Cl.$^6$ .................... A61K 31/74; A61K 7/50; A01N 59/06
[52] U.S. Cl. .................. 424/78.02; 424/682; 424/685; 424/688; 424/715; 424/717
[58] Field of Search .............. 424/401, 688, 715, 717, 424/68, 682, 685, 78.02

[56] References Cited

U.S. PATENT DOCUMENTS

| 3,608,086 | 9/1971 | Halpern | 424/317 |
| 5,182,105 | 1/1993 | Takata et al. | 424/47 |

FOREIGN PATENT DOCUMENTS

| 1088471 | 8/1958 | Germany . |
| 0150250 | 7/1985 | Japan . |
| 62-195321 | 8/1987 | Japan . |
| 63-145220 | 6/1988 | Japan . |
| 62-258806 | 10/1988 | Japan . |

Primary Examiner—Thurman K. Page
Assistant Examiner—Peter Kulkosky
Attorney, Agent, or Firm—Oblon, Spivak, McClelland, Maier & Neustadt

[57] ABSTRACT

A bath additive composition comprises an aluminum salt and a carbonate and makes the pH of bath water 8 or higher but less than 9 when the bath additive composition is dissolved in the bath water. The bath additive composition does not damage bathtubs, bath water heating devices, or the skin of users, provides a refreshing feel to the skin after bathing, and has an excellent ability of suppressing perspiration.

21 Claims, No Drawings

BATH ADDITIVE COMPOSITION COMPRISING ALUMINUM SALT AND CARBONATE OR BICARBONATE WHICH YIELDS A BATH WATER OF PH 8 TO 9

BACKGROUND OF THE INVENTION

1. Field of the Invention

This invention relates to a bath additive composition, and more particularly to a bath additive composition which has a soothing perspiration suppressing effect. The present bath additive compositions leave a bather feeling refreshed and invigorated.

2. Related Art

To more thoroughly enjoy bathing, especially in the summer, bath additive compositions which suppress perspiration after bathing are often added to the bath water. These additives leave the bather feeling refreshed for a longer period of time after finishing bathing.

Conventionally, bath additive compositions containing a water-insoluble inorganic powder such as titanium oxide are used due to their ability to suppress perspiration after bathing and to provide a refreshing feeling to bathers. These bath additive compositions, however, have a number of drawbacks. Most notably, the inorganic powder contained in these compositions makes the bath water turbid. The inorganic powder also makes the bottom surface of the bathtub sandy.

It has been reported that a bath additive composition which contains a sodium carbonate as a base ingredient and which makes the pH of the bath water fall anywhere between 9 to 10.5 gives a refreshing feeling to the skin after bathing (Japanese Patent Application Laid Open No. 145220/1988). However, the high pH of the bath water which contains such a bath additive composition is high enough to damage bathtub finishes, bath fixtures, heating devices, and even the skin of bathers. Because of the excessively high pH which these compositions impart to bath water, such compositions are not satisfactory in the practical use.

Meanwhile, it has long been known that natural hot spring water contains aluminum salts and provides certain refreshing effects. Therefore, a variety of bath additive compositions containing aluminum salts have been developed to duplicate the refreshing effects similar to those which are experienced in natural hot springs. Additionally, in order to have an inorganic aluminum salt remain dissolved in bath water without the salt precipitating from the bath water, it has been proposed to incorporate hydroxycarboxylic acid, oxalic acid or the like into the bath additive composition. (Japanese Patent Application Laid Open Nos. 195321/1987 and 258806/1988).

Such conventional bath additive compositions, however, do not satisfactorily control the pH of the bath water, and therefore, they cannot successfully solve the conventional problems which include damage to bathtub finishes and bath fixtures, as well as damage to the skin of the bather.

SUMMARY OF THE INVENTION

It is therefore an object of the present invention to provide an improved bath additive composition which has no adverse effect to bathtubs, bathing fixtures, heating devices and even to the skin of bathers, and which is capable of giving a refreshing feel to users during and after bathing.

This invention provides a bath additive composition which comprises an aluminum salt and a carbonate, and which makes the pH of bath water fall within the range of 8 to 9 when the composition is dissolved in bath water.

The bath additive composition according to the present invention does not damage bathtubs, bathing fixtures, or heating devices of bath water. Moreover, the presently claimed composition does not injure the skin of bathers. Simultaneously, the present bath additive provides a refreshing feel to the skin during and after bathing, and has an excellent perspiration suppressing effect.

DETAILED DESCRIPTION OF THE PREFERRED EMBODIMENTS

Examples of aluminum salts suitable for use in the present invention include inorganic aluminum salts such as potassium aluminum sulfate, ammonium aluminum sulfate and aluminum chloride; and soluble aluminum carboxylates such as aluminum lactate, aluminum citrate and aluminum maleate.

Regarding these aluminum salts, it is preferred that 90% by weight (hereinafter referred to as "%") or more of their particles have diameters of 200 micrometers or less. If the particles fall outside this range, a pleasant feeling during bathing is not obtained because insoluble substances and deposits are produced when the bath additive composition is dissolved in the bath water. It is preferred that 90% or more of the particles which make up the composition have diameters of 200 micrometers or less, and, more preferably, that the average particle diameter falls within a range of 20–150. Ideally, the average particle diameter should be between 20 and 100 micrometers.

These aluminum salts can be used singly or in combination. It is preferred that the aluminum salts be incorporated into the bath additive composition in the range of 0.5–20%, preferably from 1–10% and more preferably from 1–5%, based on the total amount of the bath additive composition. Preferably, the concentration of aluminum salts within the bath water should fall within 0.5–80 ppm, more preferably 1–40 ppm. If the concentration is less than 0.5 ppm, a refreshing feeling is not imparted to the bather. If the concentration exceeds 80 ppm, insoluble substances precipitate out of the bath water.

Examples of carbonates suitable for use in the present invention include sodium carbonate, potassium carbonate, sodium bicarbonate, potassium bicarbonate, and sodium sesquicarbonate. Among them, sodium carbonate and sodium bicarbonate are preferred. It is preferred that the carbonates be incorporated in the bath additive composition in an amount of 10–98%, preferably 30–90%, based on the total amount of the bath additive composition. Further, it is preferred that the concentration of the carbonates in the bath water is 10 ppm or higher, preferably within the range of 10–400 ppm, and more preferably within 30–400 ppm. If the concentration is less than 10 ppm, a refreshing feeling is not imparted to the bather.

It is preferred that the bath additive composition according to the present invention be prepared and used so that the pH of the bath water falls between 8 and 9, and preferably within 8.0–8.5, when the bath additive composition is dissolved in the bath water. If the pH of the bath water is lower than 8, the ratio of bicarbonate ions (HCO3—) and carbonate ions (CO3 2—) in the bath water becomes too low, as a result of which a refreshing feeling is not imparted to the skin. If the pH of bath water exceeds 9, the bath water damages bathtubs, bathing fixtures, and the skin of the bather. No limitation is imposed on the method of adjusting the pH of bath water. For example, the pH of bath water can be adjusted by changing the ratio of the above-mentioned essential components and the optional ingredients described hereinafter which are incorporated into the bath additive. The amounts of the above essential components are adjusted such that the pH of an aqueous 0.01% solution (40° C.) of the bath additive composition falls between 8 and 9.

The pH measurement is carried out in the following manner: 5 liters of standard water at 40° C. is placed into a 5-liter beaker immediately before the measurement. 0.5 g of a bath additive composition is then dissolved in the standard water to prepare a 0.01% solution. In cases where the bath additive composition is tabletted, it is milled with a mortar to obtain broken pieces from which a piece of about 0.3 to 0.5 g is selected, and the weight of the selected pieces is accurately measured. The amount of water necessary to yield a 0.01% solution is then poured into a 5-liter beaker into which the selected piece has been placed. After dissolution, the water is stirred to obtain a uniform solution, and the pH of the solution is measured according to the "General Tests" contained in the Japanese Pharmacopoeia.

The standard water used here is prepared by a method in which 73.36 mg of $CaCl_2.2H_2O$ is dissolved in 5 liters of ion-exchanged water and 83.83 g of sodium bicarbonate is further dissolved therein. Immediately after the dissolution of the sodium bicarbonate, carbon dioxide is blown into the water to adjust the pH of the water to 7.0.

In bath additive compositions according to the present invention, it is preferred that fumaric acid, a dicarboxylic acid represented by the following formula (I), or a water-soluble polymer be incorporated in the bath additive compositions for preventing the agglomeration and precipitation of the bath additive composition:

$$HOOC(CH_2)_L COOH \quad (I)$$

wherein L is a number of 2 to 5.

Examples of the above-mentioned dicarboxylic acid include succinic acid and adipic acid. It is preferred that the carboxylic acid be incorporated into the bath additive composition of the present invention in an amount of 1–30%, preferably 5–20%, based on the total amount of the bath additive composition.

The preferred water-soluble polymers are neutral polymers such as polyethylene glycol, polyvinyl alcohol, carboxymethylcellulose, hydroxypropylcellulose, gum arabic, gelatin, carrageenan, locust bean gum, tragacanth gum, and tamarind gum. These water-soluble polymers can be used singly or in combination, and are present in the compositions in the amount of 0.05 to 20 times by weight relative to the weight of the aluminum salt, preferably 1 to 15 times by weight, and more preferably 6 to 13 times by weight.

The bath additive compositions according to the present invention may also contain a cationized polymer or a compound which imparts a cool sensation to the skin in order to improve the refreshing feeling imparted to the bather.

The preferred cationized polymers are water-soluble cationized polymers, examples of which include cationized cellulose such as cellulose containing a quaternary ammonium group, cationized dextrin such as dextrin containing a quaternary ammonium group, chitosan, cationized vinyl pyrrolidone polymer, and N,N-dimethyl-3,5-methylene piperidinium chloride polymer.

These cationized polymers can be used singly or in combination. It is preferred that the amount of these polymers be adjusted such that the concentration of the cationized polymers in the bath water falls within the range of 0.05 to 100 ppm, preferably, 0.1 to 25 ppm. This amount of cationized polymer incorporated into the present bath additive composition may be varied relative to the amount of the bath additive composition which is used. Generally, the preferred amount is 0.01 to 20%, relative to the total amount of the bath additive composition, .preferably 0.05 to 10%, and more preferably 0.05 to 1%.

Examples of compounds which impart a cool sensation to the skin include:

(1) L-menthol, camphor and thymol;
(2) derivatives of menthol represented by the following formula,

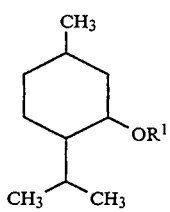

wherein $R^1$ represents a $C_1$-$C_8$ alkyl group, a monosaccharide residual group, and groups of the following formulae:

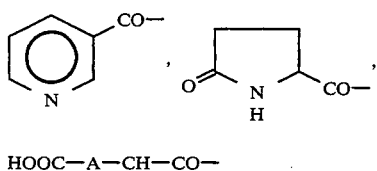

wherein A represents a single bond or $C_1$-$C_8$ alkylene group, $R^2$ represents a $C_1$-$C_8$ alkyl group, or HOOC—$(CH_2)_m$—CO—, and m represents a number from 0 to 6;

(3) compounds represented by the following formula,

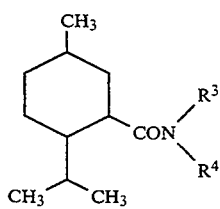

wherein $R^3$ and $R^4$ individually represent a hydrogen atom, $C_1$-$C_8$ alkyl group or hydroxy alkyl group;

(4) monocyclic compounds represented by the following formula,

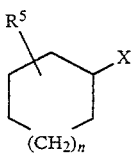

wherein X represents —OH, —COOH

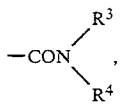

wherein $R^3$ and $R^4$ have the same meaning as defined above, $R^5$ represents a hydrogen atom or $C_1$–$C_8$ alkyl group, and n is a number from 0 to 5, (5) bicyclic compounds represented by the following formula,

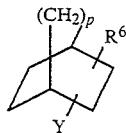

wherein Y represents —OH, —COOH or —COOR$^2$, $R^2$ has the same meaning as described above, $R^6$ represents a hydrogen atom, or $C_1$–$C_8$ alkyl group, and p is 1 or 2, (6) tricyclic compounds represented by the following formula,

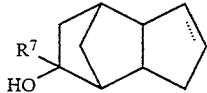

wherein $R^7$ represents a $C_1$–$C_8$ hydrocarbon group, and a broken line shows a single bond or double bond; or tricyclic compounds represented by the following formula,

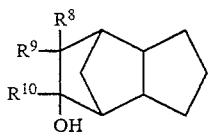

wherein one of $R^8$ and $R^9$ represents a hydrogen atom and the other represents a $C_1$–$C_8$ hydrocarbon group, or $R^8$ and $R^9$ individually represent a $C_1$–$C_8$ hydrocarbon group, or $R^8$ and $R^9$ form a ring having 2 to 6 carbon atoms; and $R^{10}$ represents a hydrogen atom or $C_1$–$C_8$ hydrocarbon group; and (7) tricyclic amides represented by the following formula,

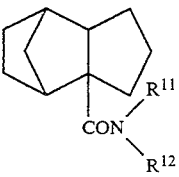

wherein $R^{11}$ and $R^{12}$ may be the same or different and individually represent a hydrogen atom, hydrocarbon which may be substituted by a hydroxy group, lower alkoxy group or lower alkoxycarbonyl group, or phenyl group substituted by a hydroxy group or a lower alkoxy group, or $R^{11}$ and $R^{12}$ together form, along with the nitrogen atom to which they are attached, a ring having 2 to 6 carbon atoms which may optionally contain an oxygen atom.

It is preferred that these cool sensation imparting agents be incorporated into the bath additive composition in an amount of 0.03 to 3%, preferably 0.3 to 2%, and more preferably 0.5 to 1% relative to the total amount of the bath additive composition. Further, the amount of the cool sensation imparting agents should be determined in such a way that the concentration to be added in the bath water falls within a range of 0.03 to 10 ppm, preferably, 0.3 to 8 ppm, and more preferably within 0.5 to 5 ppm when the bath additive composition is dissolved in the bath water.

The present bath additive composition may contain the following optional ingredients if desired:

(a) inorganic acids such as boric acid, metasilicic acid and silicic anhydride;

(b) inorganic salts such as sodium chloride, sodium sulfate, potassium nitrate, sodium nitrate, calcium nitrate, sodium polyphosphate, ammonium chloride, ferrous sulfate, sodium phosphate and sodium thiosulfate;

(c) crude drugs such as atractylodes rhizoma, atractylodes macrocephala, Japanese valerian, nepeta japonica, magnolia bark, cnidium rhizoma, bitter orange peel, ligusticum, powdered ginger, ginseng, cinnamon, paeoniae radix, peppermint leaves, scutellariae radix, gardenias fructus, tackahoe, angelicae tuhou radix, calamus root, artemisias argyi folium, schisandra repanda, angelica dahurica root, houttuynia cordata, borneol, suffron crocus, phellodendron extract, citrus unshiu peel, fennel, citri pericarpium pulveratum, camomile, melissa, rosemary, horse chestnut, milfoil and mountain arnica.

(d) oils and fats such as isopropylpalmitate, isopropylmyristate, cholesteryl isostearate, squalane, tri(caprylcapric acid) glycerol, rice-bran oil, rice-bran extract, 1-isostearoyl-3-myristoyl-glycerol, olive oil, jojoba oil, soybean oil, liquid paraffin and white Vaseline;

(e) alcohols such as ethanol, stearyl alcohol, isopropyl alcohol, cetyl alcohol and hexadecyl alcohol;

(f) polyols such as glycerol, propylene glycol and sorbitol;

(g) surfactants such as alkyl sulfate, polyoxyethylene alkyl ether sulfate, lauric acid diethanolamide, polyoxyethylene alkyl ether, polyethylene glycol monostearate; and (h) other ingredients such as titanium oxide, zinc oxide, talc, sulfur, ore sand, neutral terra abla, sodium salicylate, yolk powder, parched rice-bran, mica powder and powdered skim milk.

The bath additive compositions of this invention may further include preservatives, moisturizers, metal sequestering and chelating agents, perfumes and other ingredients.

The bath additive compositions of the present invention are prepared by conventional methods to form powders, granules, tablets and the like.

The bath additive composition according to this invention has no adverse effects to bathtubs, bath fixtures, bath water heating devices or the skin of bathers, gives a refreshing feel to the skin during and after bathing, and has an excellent perspiration suppressing effect.

EXAMPLES

The present invention will now be described in detail with reference to preferred embodiments. The following Exampels are for illustration only, and should not be construed to limit the scope of the present invention in any way.

EXAMPLES 1 TO 4

The bath additive compositions shown in Table 1 were prepared, and each dissolved in water (40° C.) to obtain a 0.01% solution.

10 panelists carried out the following evaluation test in a room at 28° C. and 70% relative humidity: Each panelist put one of his or her forearms into the solution for 5 minutes, and took the forearm therefrom to evaluate the refreshing feel to the skin. The refreshing feel thus evaluated represents "refreshing feel after bathing", shown in the bottom row of Table 1. This value was determined in accordance with the following evaluation criteria:

5: Very refreshing
4: Refreshing
3: Somewhat refreshing
2: Not refreshing
1: Far from refreshing The results are shown in Table 1, where the average values of the evaluation points are given.

| | Present Bath Add. Compositions | | | | | Comp. Bath Add. Compositions (wt. %) | | | |
|---|---|---|---|---|---|---|---|---|---|
| | 1 | 2 | 3 | 4 | 5 | 1 | 2 | 3 | 4 |
| Sodium carbonate | 40 | 30 | 30 | 40 | 45 | 40 | 30 | 10 | — |
| Sodium bicarbonate | 50 | 50 | 30 | 15 | 15 | 50 | 50 | 40 | — |
| Alum | 10 | 5 | 5 | 3 | 1 | — | — | 5 | 20 |
| Sodium sulfate | — | 15 | — | — | — | 10 | 15 | — | 80 |
| Polyethylene glycol (Ave. molecular weight: 6000) | — | — | 35 | 22 | 22 | — | 5 | — | — |
| Succinic acid | — | — | — | 15 | 14 | — | — | 14 | — |
| Sorbitol | — | — | — | 5 | 3 | — | — | — | — |
| Colorant | trace | | | | | trace | | | |
| Perfume | trace | | | | | trace | | | |
| pH (0.01%)*[1] | 8.5 | 8.3 | 8.4 | 8.4 | 8.4 | 8.9 | 8.6 | 6.4 | 6.7 |
| Refreshing feel after bathing | 4.8 | 4.7 | 4.7 | 4.7 | 4.8 | 3.2 | 3.3 | 3.2 | 3.3 |

*[1]: pH was measured in the same manner as the above.

Test Example 1

The present bath additive composition 1 and the comparative bath additive composition 1, shown in Table 1, were separately dissolved in bath water (30 g each per bath). Ten (10) panelists took a bath by laying their bodies in the bath water, and, after bathing, they compared the refreshing feeling imparted to the skin by the compositions. Results are shown in Table 2, wherein the results are indicated by the number of panelists.

TABLE 2

| | |
|---|---|
| Present bath additive composition 1 provided more refreshing feel | 5 |
| Present bath additive composition 1 provided slightly more refreshing feel | 3 |
| Did not find difference | 1 |
| Comparative bath additive composition 1 provided slightly more refreshing feel | 1 |
| Comparative bath additive composition 1 provided more refreshing feel | 0 |

Test Example 2

The present bath additive composition 2 and the comparative bath additive composition 2, shown in Table 1, were separately dissolved in bath water (30 g each per bath). Ten (10) panelists took a bath by laying their bodies in the bath water, and, after bathing, they compared the refreshing feeling imparted to the skin by the compositions. Likewise, the present bath additive composition 3 and comparative bath additive composition 3, shown in Table 1, were separately dissolved in bath water (30 g each per bath), and the same procedure as above was followed. Results are shown in Tables 3 and 4, wherein the results are indicated by the number of panelists.

TABLE 3

| | |
|---|---|
| Present bath additive composition 2 provided more refreshing feel | 4 |
| Present bath additive composition 2 provided slightly more refreshing feel | 3 |
| Did not find difference | 2 |
| Comparative bath additive composition 2 provided slightly more refreshing feel | 1 |
| Comparative bath additive composition 2 provided more refreshing feel | 0 |

TABLE 4

| | |
|---|---|
| Present bath additive composition 3 provided more refreshing feel | 3 |
| Present bath additive composition 3 provided slightly more refreshing feel | 3 |
| Did not find difference | 3 |
| Comparative bath additive composition 3 provided slightly more refreshing feel | 1 |
| Comparative bath additive composition 3 provided more refreshing feel | 0 |

Test Example 3

Healthy men carried out the test. Part of the forearm of each man (hereinafter referred to as "test portion") was contacted with a sample solution in a cup (cup method) in which each of the compositions shown in Table 5 were dissolved (40° C., 5 ml of 0.01% solution) for 10 minutes. After the test portion was towel-dried, a 5% iodine-alcohol solution was applied thereto, followed by drying. Each individual was made to perspire for 10 minutes in a room of 40° C. and 40%RH, with a starch slide attached to the test portion.

The number of sudoriferous glands indicated by color was measured in a predetermined area of 3.14 cm$^2$.

Sweat suppression rate was calculated according to the following equation:

$$\text{Sweat suppression rate (\%)} = \left|1 - \frac{\text{Number of sudoriferous glands perspired in the test portion}}{\text{Number of sudoriferous glands perspired in the comparative portion}}\right| \times 100$$

TABLE 5

| | Sweat suppression rate |
|---|---|
| Present bath additive composition 1 | 22.4 (%) |
| Comparative bath additive composition 1 | −8.9 |
| Comparative bath additive composition 4 | 7.1 |

The comparative portion was exposed to warm water (40° C.) which did not contain any additives.

As clearly shown in Table 5, the present bath additive composition exhibits an excellent perspiration suppression effect, while the comparative bath additive composition exhibits little sweat suppression effect. This sweat suppressing effect of the present invention gives an excellent refreshing feeling to bathers.

EXAMPLES 6 TO 8

The bath additive compositions shown in Table 6 were prepared by a known method to obtain powders thereof, and 30 g of each of the powders was dissolved in 150 liters of bath water (40° C.) for evaluation. 10 panelists laid their bodies in the bath water to evaluate the feel to the skin during bathing. Further, they evaluated the condition of the bath water at the time the powders were dissolved, and on the following day. The results are shown in Table 6. The average values of the points are given for the evaluation of feel to the skin.

Evaluation Criteria for feel to the skin during bathing:
5: Very good
4: Good
3: Slightly good
2: Scarcely good
1: Not good

TABLE 6

| | (parts by weight) Present Bath Compositions | | |
|---|---|---|---|
| Ingredients | 6 | 7 | 8 |
| Sodium carbonate | 30 | 45 | 45 |
| Sodium bicarbonate | 30 | 15 | 15 |
| Alum*2 | 5 | 3 | 2 |
| Polyethylene glycol*3 | 35 | 23 | 24 |
| Succinic acid | — | 14 | 14 |
| Colorant | trace | trace | trace |
| Perfume | trace | trace | trace |
| pH (0.01%) | 8.4 | 8.4 | 8.4 |
| When dissolved in bath water | | | |
| Float on bath water | none | none | none |
| Deposits | none | none | none |
| Deposits on the following day | none | none | none |
| Skin sensation during bathing | 4.7 | 4.6 | 4.7 |

*2: 90% or more particles are 200 micrometers or smaller (burnt alum, average particle diameter: 30 micrometers, product of Taiho Chemical Co.)
*3: average molecular weight: 6000

As clearly shown in Table 6, the bath additive compositions containing aluminum salts having a particle size falling within the stated range and which contain a water-soluble polymer did not deposit when dissolved in the bath water, and remained dissolved in the bath water for at least 24 hours following dissolution. The Table shows that the presently claimed bath additive provides an excellent feeling to the skin during bathing.

EXAMPLES 9 TO 12

The bath additive compositions shown in Table 7 were prepared by a known method to evaluate skin sensation. 3 g of each powder were separately dissolved in 15 liters of bath water (40° C.). 10 panelists carried out the following evaluation test in a room at 28° C. and 70% relative humidity: Each panelist put his or her forearm into the bath water for 5 minutes. They evaluated the gentle feel to the skin during the immersion. The feel to the skin thus evaluated represents the "gentle feel to the skin during bathing" included in Table 7. Further, they took their forearm out from the water, and towel dried to evaluate the refreshing feel to the skin. The refreshing feel thus evaluated represents "refreshing feel after bathing" included in Table 7. The results are shown in Table 7, in which the results are presented as the average value of points determined in accordance with the following evaluation criteria.

Evaluation Criteria
5: Excellent
4: Good
3: Moderate
2: Poor
1: Very poor and unfavorable feeling As is clearly Shown in Table 7, all of the present bath additive compositions provide a gentle feel to the skin during bathing and refreshing feeling after bathing. To the contrary, none of comparative compositions gave a gentle feel to the skin during bathing or refreshing feeling after bathing.

Test Example 4

The present bath additive composition 9 and comparative bath additive composition 5 were separately dissolved in bath water (30 g each per bath). 10 panelists took a bath by laying their bodies in the bath water, and, after bathing, they compared the compositions in terms of the "gentle feel during bathing" and "refreshing feel after bathing". Results are shown in Table 8, wherein the results are indicated by the number of panelists.

TABLE 7

| | Present Bath Add. Compositions | | | | (Parts by weight) Comparative Bath Add. Compositions | | | |
|---|---|---|---|---|---|---|---|---|
| Ingredients | 9 | 10 | 11 | 12 | 5 | 6 | 7 | 8 |
| Sodium carbonate | 40 | 30 | 30 | 45 | 40 | 30 | 10 | 40 |
| Sodium bicarbonate | 50 | 50 | 30 | 15 | 50 | 50 | 40 | 50 |
| Alum | 10 | 5 | 5 | 3 | — | — | 5 | — |

TABLE 7-continued

|  | Present Bath Add. Compositions | | | | (Parts by weight) Comparative Bath Add. Compositions | | | |
|---|---|---|---|---|---|---|---|---|
| Ingredients | 9 | 10 | 11 | 12 | 5 | 6 | 7 | 8 |
| Cationized cellulose*4 | 0.2 | 0.2 | 0.1 | 0.2 | — | — | — | 0.2 |
| Sodium sulfate | — | 15 | 35 | — | 10 | 15 | — | 10 |
| Polyethylene glycol | — | — | — | 23 | — | 5 | — | — |
| Succinic acid | — | — | — | 14 | — | — | 45 | — |
| Colorant | trace | trace | trace | trace | trace | trace | trace | trace |
| Perfume | trace | trace | trace | trace | trace | trace | trace | trace |
| pH (0.01%) | 8.5 | 8.3 | 8.4 | 8.4 | 8.9 | 8.6 | 6.4 | 8.9 |
| Gentle feel during bathing | 4.8 | 4.8 | 4.8 | 4.8 | 2.1 | 3.0 | 2.5 | 3.5 |
| Refreshing feel after bathing | 4.7 | 4.6 | 4.7 | 4.7 | 3.3 | 2.8 | 2.5 | 2.2 |

*4: hydroxyethyl cellulose hydroxytrimethyl ammonium chloride ether (Cati-cello H-60, trademark, product of Kao Corp.)

TABLE 8

|  | Gentle feel during bathing | Refreshing feel after bathing |
|---|---|---|
| Present bath additive comp. 9 feels better | 6 | 5 |
| Present bath additive comp. 9 feels slightly better | 2 | 3 |
| Did not find difference | 2 | 1 |
| Comparative bath additive comp. 5 feels slightly better | 0 | 1 |
| Comparative bath additive comp. 5 feels better | 0 | 0 |

Test Example 5

The same procedure as described in Test Example 4 was followed using bath additive compositions of Example 10, Comparative Example 6, Example 11 and Comparative Example 7. The composition of Example 10 was compared with Comparative Example 6 and the composition of Example 11 was compared with Comparative Example 7 in terms of the gentle feel during bathing and the refreshing feeling after bathing. Results are shown in Tables 9 and 10, wherein the results are indicated by the number of panelists.

TABLE 9

|  | Gentle feel during bathing | Refreshing feel after bathing |
|---|---|---|
| Present bath additive composition 10 is better | 6 | 4 |
| Present bath additive comp. 10 is slightly better | 3 | 3 |
| Did not find difference | 1 | 2 |
| Comparative bath additive comp. 6 is slightly better | 0 | 1 |
| Comparative bath additive composition 6 is better | 0 | 0 |

TABLE 10

|  | Gentle feel during bathing | Refreshing feel after bathing |
|---|---|---|
| Present bath additive composition 11 is better | 5 | 3 |
| Present bath additive comp. 11 is slightly better | 3 | 3 |
| Did not find difference | 1 | 3 |
| Comparative bath additive comp. 7 is slightly better | 1 | 1 |
| Comparative bath additive composition 7 is better | 0 | 0 |

EXAMPLES 13 AND 14

The bath additive compositions shown in Table 11 were prepared by a known method to evaluate the sweat suppression rate and refreshing feeling after bathing.

Evaluation Method Sweat Suppression Rate:

Healthy men carried out the test. Part of the forearm of each man (hereinafter referred to as the "test portion") was contacted with a sample solution in a cup (cup method) in which each of the compositions was dissolved (40° C., 5 ml of 0.01% solution) for 10 minutes. After the test portion was towel dried, a 5% iodine-alcohol solution was applied thereto, followed by drying. Each individual was made to perspire for 10 minutes in a room of 40° C. and 40%RH, with a starch slide attached to the test portion.

The number of sudoriferous glands indicated by color was measured in a predetermined area of 3.14 $cm^2$.

Sweat suppression rate was calculated according to the following equation.

$$\text{Sweat suppression rate (\%)} = \left| 1 - \frac{\text{Number of sudoriferous glands perspired in the test portion}}{\text{Number of sudoriferous glands perspired in the comparative portion}} \right| \times 100$$

The comparative portion was exposed to warm water (40° C.) which did not contain any additives.

Refreshing feel after bathing:

10 panelists carried out the following evaluation test in a room at 28° C. and 70% relative humidity: Each panelist put his or her forearm into the bath water (40° C.) for 5 minutes. They took their forearm out from the water, and evaluated the refreshing feeling to the skin. The refreshing feeling thus evaluated represents "refreshing feel after bathing". The results are shown in Table 11, in which the results are presented as the average value of points determined in accordance with the following evaluation criteria.

5: Very refreshing
4: Refreshing
3: Somewhat refreshing
2: Not refreshing
1: Far from refreshing and unfavorable heavy feel.

TABLE 11

| Ingredients | Present Bath Compositions (wt %) | |
|---|---|---|
| | 13 | 14 |
| L-menthol | 0.7 | 0.7 |
| Sodium bicarbonate | 50 | 50 |
| Sodium carbonate | 40 | 40 |
| Burnt alum | 8 | — |
| Aluminum lactate | — | 8 |
| Sorbitol | suitable amount | suitable amount |
| Colorant | trace | trace |
| Perfume | trace | trace |
| pH (0.01%) | 8.4 | 8.4 |
| Sweat suppression rate (%) | 33 | 35 |
| Refreshing feel after bathing | 4.7 | 4.8 |

What is claimed as new and desired to be secured by Letters Patent of the United States of America is:

1. A bath additive composition comprising (a) from 1 to 10 wt. % of an aluminum salt and (b) from 10 to 98 wt. % of a bicarbonate or carbonate, wherein a 0.01% by weight solution of said composition in water gives a pH of 8 to 9, said water having a pH of 7.0, wherein said bath composition imparts an improved gentle feel to the skin during bathing and an improved refreshing feel after bathing.

2. The bath additive composition of claim 1, wherein said 0.01% by weight solution of said composition in said water gives a pH of 8–8.5.

3. The bath additive composition of claim 1, wherein said aluminum salt is selected from the group consisting of potassium aluminum sulfate, ammonium aluminum sulfate, aluminum chloride, aluminum lactate, aluminum citrate and aluminum maleate.

4. The bath additive composition of claim 1, wherein said carbonate is selected from the group consisting of sodium carbonate, sodium bicarbonate, potassium carbonate, potassium bicarbonate and sodium sesquicarbonate.

5. The bath additive composition of claim 4, wherein said carbonate is selected from the group consisting of sodium carbonate and sodium bicarbonate.

6. The bath additive composition of claim 1, further comprising a fumaric acid or a dicarboxylic acid represented by the following formula (I),

$$HOOC(CH_2)_L COOH \qquad (I)$$

wherein L is a number of 2 to 5.

7. The bath additive composition of claim 6, wherein said dicarboxylic acid represented by formula (I) is selected from the group consisting of succinic acid and adipic acid.

8. The bath additive composition of claim 7, wherein said fumaric acid, or said dicarboxylic acid of formula (I) is present in an amount of from 1–30 wt % of the total bath additive composition.

9. The bath additive composition of claim 1, further comprising a water-soluble polymer.

10. The bath additive composition of claim 9, wherein said water-soluble polymer is selected from the group consisting of polyethylene glycol, polyvinyl alcohol, carboxymethyl cellulose, hydroxypropyl cellulose, gum arabic, gelatin, carrageenan, lowcast bean gum, tragacanth gum, and tamarind gum.

11. The bath additive composition of claim 1, wherein said water-soluble polymer is present in an amount of from 0.05 to 20 times the weight of aluminum salt in said bath additive composition.

12. The bath additive composition of claim 1, further comprising a cationized polymer.

13. The bath additive composition of claim 12, wherein said cationized polymer is selected from the group consisting of cationized cellulose, cationized dextrin, chitosan, cationized vinyl pyrrolidone polymer, and N,N-dimethyl-3,5-methylene piperidinium chloride polymer.

14. The bath additive composition of claim 13, wherein said cationized polymer is present in an amount of from 0.01–20 wt % of the total bath additive composition.

15. The bath additive composition of claim 1, further comprising a cool sensation imparting agent.

16. The bath additive composition of claim 15, wherein said cool sensation imparting agent is selected from the group consisting of:

L-menthol, camphor and thymol;

derivatives of menthol represented by the following formula:

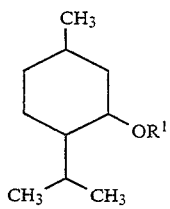

wherein $R^1$ represents a $C_1$–$C_8$ alkyl group, monosaccharide residual group and groups of the following formulae:

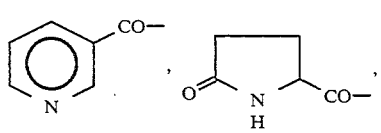

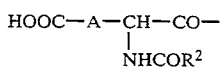

wherein A represents a single bond or a $C_1$–$C_8$ alkylene group, $R^2$ represents a $C_1$–$C_8$ alkyl group, or HOOC—$(CH_2)_m$—CO—, and m is a number from 0 to 6;

compounds represented by the following formula:

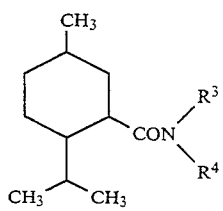

wherein $R^3$ and $R^4$ individually represent a hydrogen atom, $C_1$–$C_8$ alkyl group or a hydroxy alkyl group;

monocyclic compounds represented by the following formula:

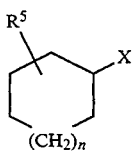

wherein X represents —OH, —COOH or

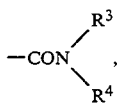

$R^3$ and $R^4$ have the same meaning as defined above, $R^5$ represents a hydrogen atom or $C_1$-$C_8$ alkyl group, and n is an integer from 0 to 5;

bicyclic compounds represented by the following formula:

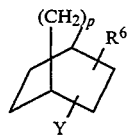

wherein Y represents —OH, —COOH or —COOR$^2$, $R^2$ has the same meaning as described above, $R^6$ represents a hydrogen atom or a $C_1$-$C_8$ alkyl group, and p is a number from 1 or 2;

tricyclic compounds represented by the following formula:

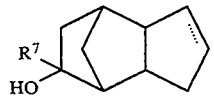

wherein $R^7$ represents a $C_1$-$C_8$ hydrocarbon group, and a broken line shows a single bond or double bond;

tricyclic compounds represented by the following formula:

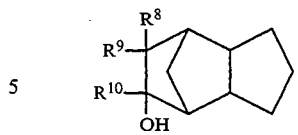

wherein one of $R^8$ and $R^9$ represents a hydrogen atom and the other represents a $C_1$-$C_8$ hydrocarbon group, or $R^8$ and $R^9$ both individually represent a $C_1$-$C_8$ hydrocarbon group, or $R^8$ and $R^9$ together form a ring having 2 to 6 carbon atoms; and $R^{10}$ represents a hydrogen atom or a $C_1$-$C_8$ hydrocarbon group; and tricyclic amides represented by the following formula:

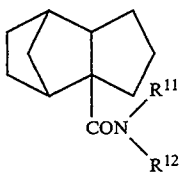

wherein $R^{11}$ and $R^{12}$ may be the same or different and individually represent a hydrogen atom, hydrocarbon, hydroxy-substituted hydrocarbon, lower alkoxy-substituted hydrocarbon, lower alkoxycarbonyl-substituted hydrocarbon, hydroxy-substituted phenyl group, lower alkoxy-substituted phenyl group, or $R^{11}$ and $R^{12}$, with the nitrogen atom to which they are attached, together form a ring having 2 to 6 carbon atoms, or a ring of 1–5 carbon atoms and one oxygen atom.

17. The bath additive composition of claim 16, wherein said cool sensation imparting agent is present in an amount of from 0.03–3.0 wt % of the total bath additive composition.

18. The bath additive of claim 17, wherein said cool sensation imparting agent is present in an amount of from 0.5–1 wt % of the total bath additive composition.

19. The bath additive composition of claim 18, wherein said cool sensation imparting agent is present in said bath additive composition such that the amount of said cool sensation imparting agent is within the range of from 0.003–10 parts per million when said bath additive composition is dissolved in bath water.

20. The bath additive composition of claim 16, wherein said cool sensation imparting agent is L-menthol.

21. The bath additive composition of claim 1, wherein said aluminum salt has a particle size distribution such that 90% by weight or more of said aluminum salt particles have diameters of 200 micrometers or less.

* * * * *